(12) United States Patent
Duffy (10) Patent No.: US 7,276,045 B2
(45) Date of Patent: Oct. 2, 2007

(54) APPARATUS AND METHOD FOR WIRE EXCHANGE

(75) Inventor: Niall Duffy, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 782 days.

(21) Appl. No.: 10/718,689

(22) Filed: Nov. 24, 2003

(65) Prior Publication Data

US 2005/0113803 A1    May 26, 2005

(51) Int. Cl.
*A61M 29/00* (2006.01)
(52) U.S. Cl. ............................ 604/103.04
(58) Field of Classification Search ........... 604/96.01, 604/103.04, 97.01, 284, 523; 606/192, 194, 606/191
See application file for complete search history.

(56) References Cited

U.S. PATENT DOCUMENTS

| | | | |
|---|---|---|---|
| 4,748,982 A | 6/1988 | Horzewski et al. |
| 4,762,129 A | 8/1988 | Bonzel |
| 4,988,356 A | 1/1991 | Crittenden et al. |
| 5,040,548 A | 8/1991 | Yock |
| 5,061,273 A | 10/1991 | Yock |
| 5,149,330 A | 9/1992 | Brightbill |
| 5,171,222 A | 12/1992 | Euteneuer et al. |
| 5,178,158 A | 1/1993 | de Toledo |
| 5,205,822 A | 4/1993 | Johnson et al. |
| 5,217,435 A | 6/1993 | Kring |
| 5,232,445 A | 8/1993 | Bonzel |
| 5,263,932 A | 11/1993 | Jang |
| 5,290,241 A | 3/1994 | Kraus et al. |
| 5,300,085 A | 4/1994 | Yock |
| 5,324,269 A | 6/1994 | Miraki |
| 5,327,885 A | 7/1994 | Griffith |
| 5,334,187 A | 8/1994 | Fischell et al. |
| 5,336,184 A | 8/1994 | Teirstein |
| 5,350,395 A | 9/1994 | Yock |
| 5,357,978 A | 10/1994 | Turk |
| 5,364,376 A | 11/1994 | Horzewski et al. |
| 5,387,226 A | 2/1995 | Miraki |
| 5,389,087 A | 2/1995 | Miraki |
| 5,409,459 A | 4/1995 | Gambale |
| 5,451,233 A | 9/1995 | Yock |
| 5,458,639 A | 10/1995 | Tsukashima et al. |
| 5,460,185 A | 10/1995 | Johnson et al. |
| 5,466,222 A | 11/1995 | Ressemann et al. |
| 5,489,271 A | 2/1996 | Andersen |
| 5,496,346 A | 3/1996 | Horzewski et al. |
| 5,501,227 A | 3/1996 | Yock |
| 5,531,690 A * | 7/1996 | Solar .................... 604/103.04 |
| 5,531,700 A | 7/1996 | Moore et al. |

(Continued)

*Primary Examiner*—Kevin T. Truong (57) ABSTRACT

The invention disclosed herein provides a catheter that acts as both a rapid-exchange (RX) catheter and a multi-exchange (MX) catheter. The catheter includes a proximal shaft, transition shaft, distal shaft, and catheter conversion shaft. Attached to the distalmost tip of the conversion shaft is a clip. The clip allows the conversion shaft to be detachably secured to the transition shaft while the catheter and a guidewire are both in situ. When the clip attaches to the transition shaft, a clip port in the clip aligns with an exchange joint in the transition shaft. In doing so, the catheter conversion shaft and a guide member act to allow the guidewire to be accessible through a guidewire exit of the guide member. The guide member is slidable along the catheter conversion shaft such that the catheter is usable as a MX catheter.

8 Claims, 12 Drawing Sheets

U.S. PATENT DOCUMENTS

| | | | |
|---|---|---|---|
| 5,549,556 A | 8/1996 | Ndondo-Lay et al. |
| 5,571,094 A | 11/1996 | Sirhan |
| 5,578,009 A | 11/1996 | Kraus et al. |
| 5,626,600 A | 5/1997 | Horzewski et al. |
| 5,685,312 A | 11/1997 | Yock |
| 5,709,658 A | 1/1998 | Sirhan et al. |
| 5,718,680 A | 2/1998 | Kraus et al. |
| 5,749,888 A | 5/1998 | Yock |
| 5,755,685 A | 5/1998 | Andersen |
| 5,769,868 A | 6/1998 | Yock |
| 5,779,671 A | 7/1998 | Ressemann et al. |
| 5,807,355 A | 9/1998 | Ramzipoor et al. |
| 5,919,164 A | 7/1999 | Andersen |
| 5,919,175 A | 7/1999 | Sirhan |
| 5,947,925 A | 9/1999 | Ashiya et al. |
| 5,947,927 A | 9/1999 | Mertens |
| 6,013,068 A | 1/2000 | Spiegelhalter |
| 6,036,715 A | 3/2000 | Yock |
| 6,056,719 A | 5/2000 | Mickley |
| 6,096,009 A | 8/2000 | Windheuser et al. |
| RE36,857 E | 9/2000 | Euteneuer et al. |
| 6,165,197 A | 12/2000 | Yock |
| 6,196,995 B1 | 3/2001 | Fagan |
| 6,299,595 B1 | 10/2001 | Dutta et al. |
| 2003/0191491 A1 | 10/2003 | Duane et al. |

\* cited by examiner

APPARATUS AND METHOD FOR WIRE EXCHANGE

BACKGROUND OF THE INVENTION

1. Field of the Invention

The present invention relates to a medical device. More specifically, the invention relates to a catheter, which may act as both a rapid exchange catheter (RX) and a multi-exchange catheter (MX).

2. Related Art

Cardiovascular disease, including atherosclerosis, is the leading cause of death in the U.S. One method for treating atherosclerosis and other forms of coronary narrowing is percutaneous transluminal coronary angioplasty, commonly referred to as "angioplasty" or "PTCA". The objective in angioplasty is to enlarge the lumen of the affected coronary artery by radial hydraulic expansion. The procedure is accomplished by inflating a balloon of a balloon catheter within the narrowed lumen of the coronary artery. Radial expansion of the coronary artery occurs in several different dimensions, and is related to the nature of the plaque. Soft, fatty plaque deposits are flattened by the balloon, while hardened deposits are cracked and split to enlarge the lumen.

One or multiple dilatations may be necessary to effectively dilate the artery. In many instances, successive dilatations using a succession of balloon catheters with balloons of increasingly larger diameters may be required. In order to accomplish the multiple dilatations, the original catheter must be removed and a second balloon catheter tracked to the lesion. When catheter exchange is desired, it is advantageous to leave the guidewire in place while the first catheter is removed in order to insert the second catheter without having to reestablish the path by inserting a new guidewire. To remove a balloon catheter while leaving the guidewire in place, there must be a portion of the guidewire extending out of the balloon catheter at the proximal end so that the guidewire can be held in place while the balloon catheter is removed.

Two types of catheters commonly used in angioplasty procedures are referred to as over-the-wire (OTW) catheters and rapid exchange (RX) catheters. A third type of catheter with preferred features of both OTW and RX catheters, that is sold under the trademarks MULTI-EXCHANGE, ZIPPER MX, ZIPPER, and/or MX is discussed below. An OTW catheter's guidewire shaft runs the entire length of the catheter and is attached to, or enveloped within, an inflation shaft. Thus, the entire length of an OTW catheter is tracked over a guidewire during a PTCA procedure. A RX catheter, on the other hand, has a guidewire shaft that extends within only the distalmost portion of the catheter. Thus, during a PTCA procedure only the distalmost portion of a rapid exchange catheter is tracked over a guidewire.

If a catheter exchange is required while using a standard OTW catheter, the user must add an extension onto the proximal end of the guidewire to maintain control of the guidewire, slide the catheter off of the extended guidewire, slide the new catheter onto the guidewire and track back into position. Multiple operators are required to hold the extended guidewire in place while the original catheter is changed out.

A RX catheter avoids the need for multiple operators when changing out the catheter and therefore is often referred to as a "single operator" catheter. With a rapid exchange catheter, the guidewire is outside the shaft of the catheter for all but the distalmost portion of the catheter. The guidewire can be held in place without an extension when the catheter is removed from the body. Once the original catheter is removed, a subsequent catheter may be threaded onto the in-place guidewire and tracked to the lesion. However, one problem associated with RX catheters is that the exposed portion of the guidewire may become tangled with the catheter shaft during use.

In addition, there are instances when the guidewire and not the catheter must be replaced. For example, the guidewire may become damaged during the procedure or it may be discovered during the procedure that a different shape, length, or size of guidewire is needed. An OTW catheter, with the guidewire lumen extending the entire length of the catheter, allows for simple guidewire exchange. With a RX catheter, the guidewire lumen does not extend the entire length of the catheter. Therefore, the guidewire, and most of the catheter, must be removed from the body in order to exchange guidewires. Essentially the procedure must then start anew because both the guidewire and the catheter must be retracked to the treatment site.

A balloon catheter capable of both fast and simple guidewire and catheter exchange is particularly advantageous. A catheter designed to address this need sold by Medtronic AVE, Inc. of Santa Rosa, Calif. under the trademarks MULTI-EXCHANGE, ZIPPER MX, ZIPPER and/or MX (hereinafter referred to as the "MX catheter") is disclosed in U.S. Pat. No. 4,988,356 to Crittenden et al., and in copending U.S. application Ser. No. 10/116,234, filed Apr. 4, 2002, both of which are incorporated in their entirety herein by reference. The MX catheter includes a catheter shaft having a cut that extends longitudinally along the catheter shaft and that extends radially from a guidewire lumen to an outer surface of a catheter shaft. A guide member through which the shaft is slidably coupled cooperates with the cut such that a guidewire may extend transversely into or out of the guidewire lumen at any location along the cut's length. By moving the shaft with respect to the guide member, the effective over-the-wire length of the MX catheter is adjustable.

When using the MX catheter, the guidewire is maneuvered through the patient's vascular system such that a distal end of the guidewire is positioned across the treatment site. With the guide member positioned near a distal end of the catheter, a proximal end of the guidewire is threaded into a guidewire lumen opening at the distal end of the catheter and out through the guide member such that the proximal end of the guidewire protrudes out a proximal end of the guide member. By securing the guide member and the proximal end of the guidewire in a fixed position, the catheter may then be transported over the guidewire by advancing the catheter toward the guide member. In doing so, as the catheter advances toward the guide member, the guidewire lumen envelops the guidewire and the catheter is advanced into the patient's vasculature. In a PTCA embodiment, the MX catheter may be advanced over the guidewire in this manner until the distal end of the catheter having the dilatation balloon is positioned within the stenosis and essentially the entire length of the guidewire is encompassed within the guidewire lumen.

Furthermore, the indwelling MX catheter may be exchanged with another catheter by reversing the operation described above. To this end, the indwelling catheter may be removed by withdrawing the proximal end of the catheter from the patient while holding the proximal end of the guidewire and the guide member in a fixed position. When the catheter has been withdrawn to the point where the distal end of the slot has reached the guide member, the distal portion of the catheter over the guidewire is of a sufficiently short length that the catheter may be drawn over the proximal end of the guidewire without releasing control of the guidewire or disturbing its position within the patient. After the catheter has been removed, another catheter may be threaded onto the guidewire and advanced over the guidewire in the same manner described above with regard to the MX catheter. The MX catheter not only permits catheter exchange without the use of the very long exchange guidewire and without requiring withdrawal of the initially placed guidewire, but it also overcomes many of the other difficulties discussed in association with RX catheters.

It is among the general objects of the invention described herein to provide a catheter, which provides all the benefits of a rapid exchange catheter and a multi-exchange catheter. Specifically, what is needed is a catheter, which allows for guidewire exchange while maintaining the in situ catheter position and catheter exchange while maintaining the in situ guidewire position. Accordingly, there arises a need for a catheter having a proximal shaft, a transition shaft, a distal shaft, an exchange joint, and a catheter conversion shaft. A preferred embodiment also includes a guide member and a longitudinal cut in the catheter conversion shaft. These features provide a user the flexibility to use the catheter both as a rapid exchange catheter and a multi-exchange catheter by converting the catheter during a procedure.

Conversion is accomplished through the attachment and detachment of the catheter conversion shaft to a rapid exchange catheter. It would be understood by one having ordinary skill in the art that the catheter conversion shaft according to the present invention can be sized and adapted to be used on any RX catheter model. The rapid exchange catheter is converted by attaching the catheter conversion shaft to the catheter, thereby extending the rapid exchange catheter's guidewire shaft and lumen and providing the user the ability to change out the guidewire while maintaining catheter position in situ. Further, the catheter is converted back to a rapid exchange catheter by detaching the catheter conversion shaft from the catheter, thereby providing the user the ability to change out the catheter while maintaining guidewire position in situ. In a preferred embodiment further including the longitudinal cut and guide member, conversion is accomplished in the same manner. However, the longitudinal cut and guide member give a user the added advantage of multiple access points to the guide wire lumen along the catheter conversion shaft. In this way, the catheter conversion shaft has a variable OTW length for ease of wire exchange.

SUMMARY OF THE INVENTION

To achieve the foregoing and other objects, and in accordance with the purposes of the present invention as embodied and broadly described herein, the catheter of the present invention provides a catheter that allows for both easy guidewire exchange and easy catheter exchange.

A catheter according to the present invention includes a catheter shaft, which is comprised of a proximal shaft, a transition shaft, and a distal shaft. The proximal shaft has a proximal end, a distal end and an inflation lumen. The proximal shaft extends from a proximal end of the catheter to a proximal end of the transition shaft. The proximal shaft inflation lumen extends longitudinally through the proximal shaft. The proximal shaft inflation lumen provides fluid communication between an inflation hub at the proximal end thereof and a transition shaft inflation lumen at the distal end thereof.

The transition shaft has a proximal end, a distal end, an inflation lumen, and an exchange joint. The transition shaft proximal end is attached to the proximal shaft distal end and the transition shaft distal end is attached to a proximal end of the distal shaft. The transition shaft inflation lumen extends longitudinally therethrough and is in fluid communication with the proximal shaft inflation lumen and a distal shaft inflation lumen. The transition shaft acts as a link connecting the proximal shaft and the distal shaft and the inflation lumens therein.

The exchange joint includes an opening in the transition shaft. A proximal end of a guidewire shaft having a guidewire lumen is attached to an inner surface of the transition shaft, around the periphery of the exchange joint. The exchange joint allows access to the guidewire lumen and acts as a proximal guidewire port.

The distal shaft has a proximal end, a distal end, an inflation lumen, and encases the guidewire shaft having the guidewire lumen. The distal shaft extends from the distal end of the transition shaft to a proximal end of a dilatation balloon. Passing longitudinally through the distal shaft is the guidewire shaft. The guidewire shaft has a proximal end and a distal end. The proximal end of the guidewire shaft is attached to the exchange joint as described above and the distal end of the guidewire shaft extends through the dilatation balloon and is bonded to a distal end of the dilatation balloon. The guidewire shaft has an inner surface and an outer surface. The guidewire shaft inner surface forms the guidewire lumen. An area between the guidewire shaft outer surface and the inner surface of the distal shaft forms the inflation lumen. In one embodiment, the distal shaft inflation lumen and guidewire lumen are co-axial and extend longitudinally through the distal shaft. The proximal end of the distal shaft is attached to the distal end of the transition shaft. The distal shaft inflation lumen is in fluid communication with the transition shaft inflation lumen. A dilatation balloon is attached to the distal shaft at the distal end thereof.

The catheter according to the present invention also includes a catheter conversion shaft. The catheter conversion shaft includes a proximal end, a distal end, and a guidewire lumen. In a preferred embodiment, the catheter conversion shaft also includes a longitudinal cut that extends longitudinally along the catheter conversion shaft and extends radially from an inner surface to an outer surface of the catheter conversion shaft. The catheter conversion shaft guidewire lumen extends longitudinally through the catheter conversion shaft. Additionally, the preferred embodiment includes a stop attached to the proximal end of the catheter conversion shaft and a clip attached to the distal end of the catheter conversion shaft. The stop is cylindrical and has a proximal end, a distal end, and an outer diameter. The stop distal end is attached to the proximal end of the catheter conversion shaft. The outer diameter of the stop is larger than an outer diameter of the catheter conversion shaft and an inner diameter of a guide member (described below), and acts to abut against a proximal end of the guide member.

The clip of the catheter conversion shaft has a proximal end, a distal end, an inner surface, an inner diameter, an outer surface, and a clip port. The clip is attached to the distal end of the catheter conversion shaft, such that the clip port is co-axial with the catheter conversion shaft guidewire lumen and thereby allows a guidewire to pass through. The clip inner diameter is substantially similar to an outer diameter of the transition shaft thereby allowing the clip to be frictionally attached to and detached from the transition shaft. It would be understood by one having ordinary skill in the art that the clip inner diameter of the present invention could be sized and adapted to be used off the shelf with any RX catheter model. When the clip is frictionally attached to the transition shaft, the clip is positioned such that the clip port aligns with the exchange joint and thereby allows a guidewire to pass from the catheter conversion shaft guidewire lumen to the distal shaft guidewire lumen and thereby forms substantially a full-length guidewire lumen.

Slidably attached to the catheter conversion shaft preferred embodiment is a guide member. The guide member has a proximal end, a distal end, and a guidewire exit. The guide member is slidable along the catheter conversion shaft from the stop at the proximal end to the clip at the distal end and is in communication with the longitudinally extending cut in the catheter conversion shaft. In this way when using the catheter conversion shaft, the position of the proximal guidewire exit may be changed by sliding the guide member along the catheter conversion shaft along the cut. The guidewire member allows a guidewire to slide into and out of the catheter conversion shaft guidewire lumen by opening the cut and providing the guidewire exit for operator access to the guidewire.

BRIEF DESCRIPTION OF THE FIGURES

The foregoing and other features and advantages of the invention will be apparent from the following, more particular description of a preferred embodiment of the invention, as illustrated in the accompanying drawings.

DETAILED DESCRIPTION OF THE INVENTION

A preferred embodiment of the present invention is now described with reference to the figures where like reference numbers indicate identical or functionally similar elements. Also in the figures, the left most digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing from the spirit and scope of the invention.

Figure 1:
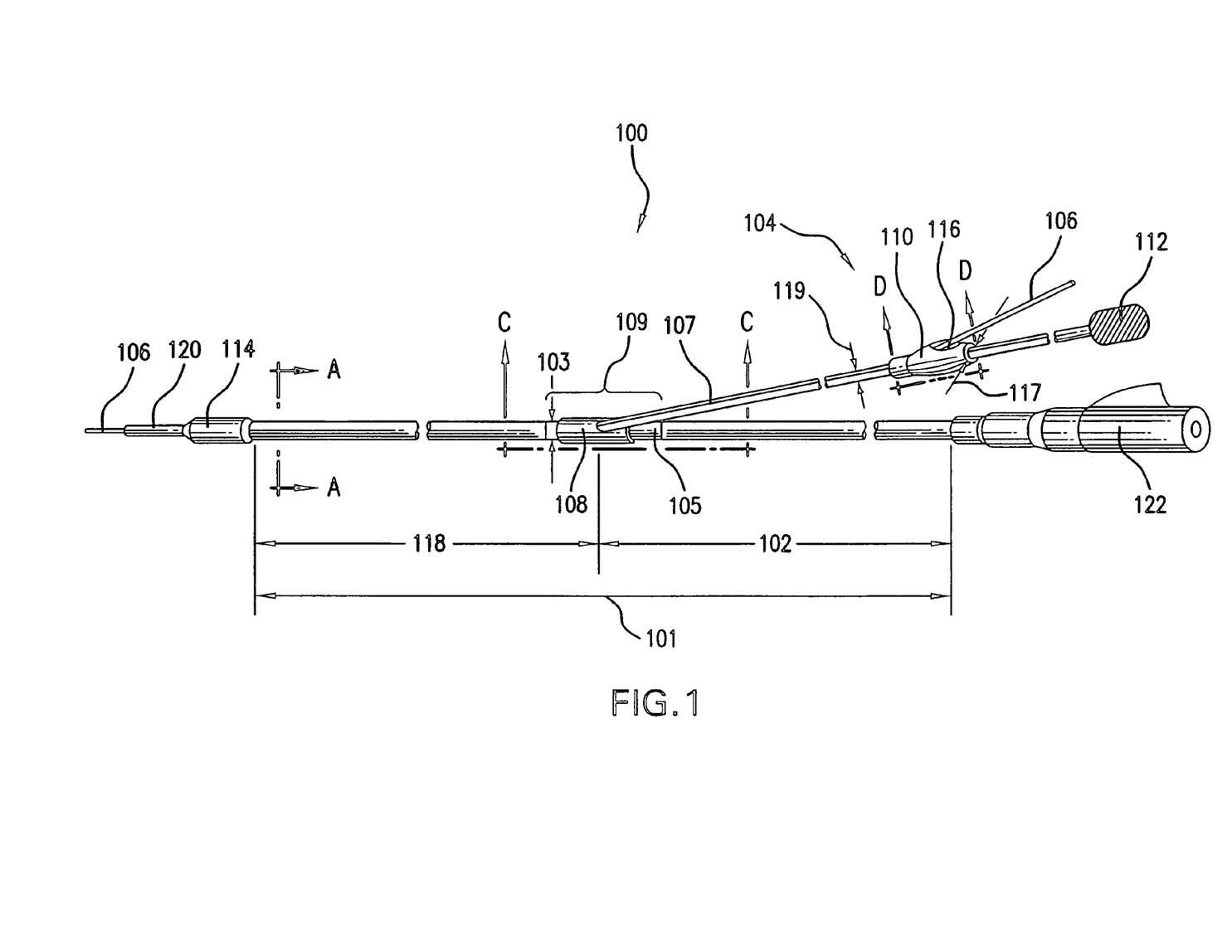
FIG. 1 is a perspective view of a preferred embodiment of a catheter according to the present invention.
Figure 1A:
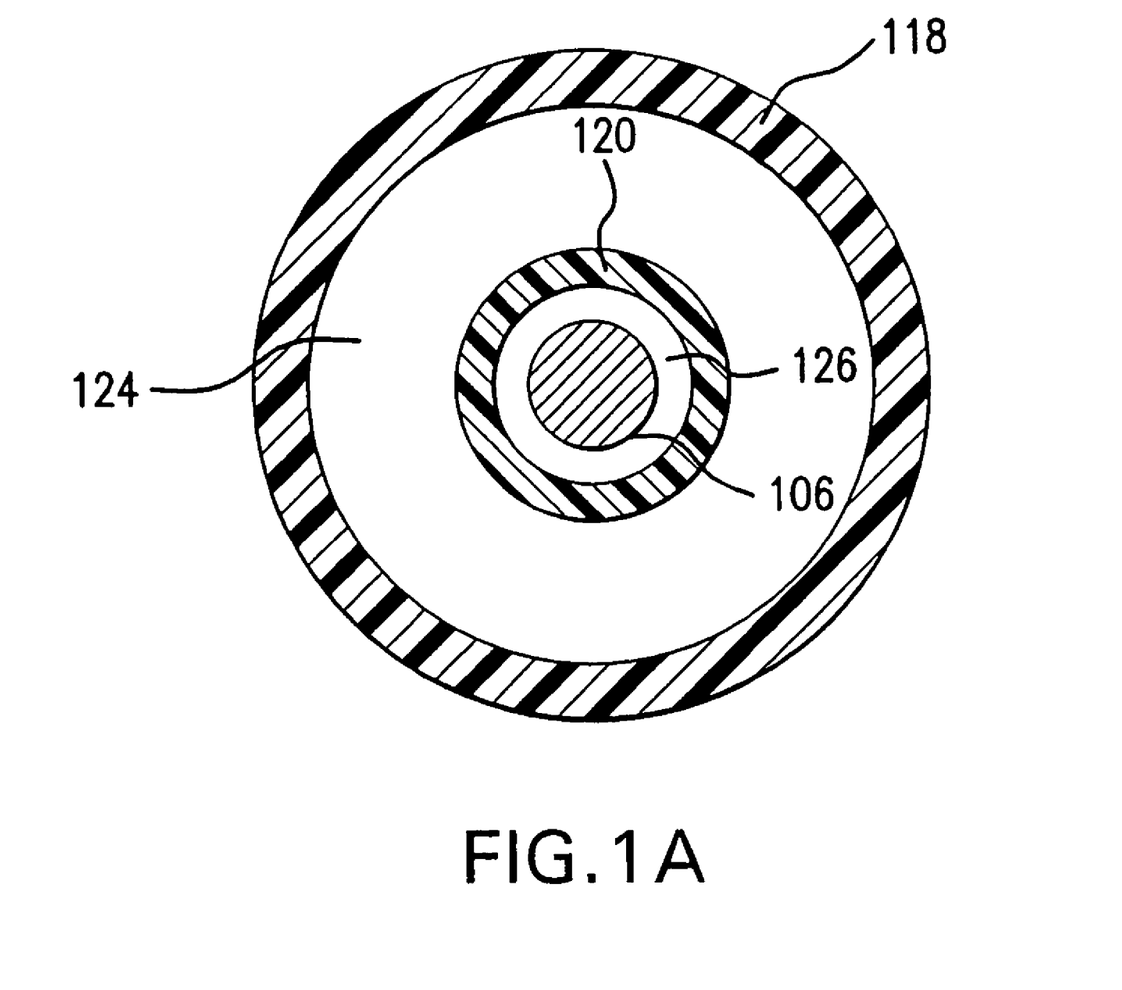
FIG. 1A is a cross-sectional view along line A-A in FIG. 1.
Figure 2:
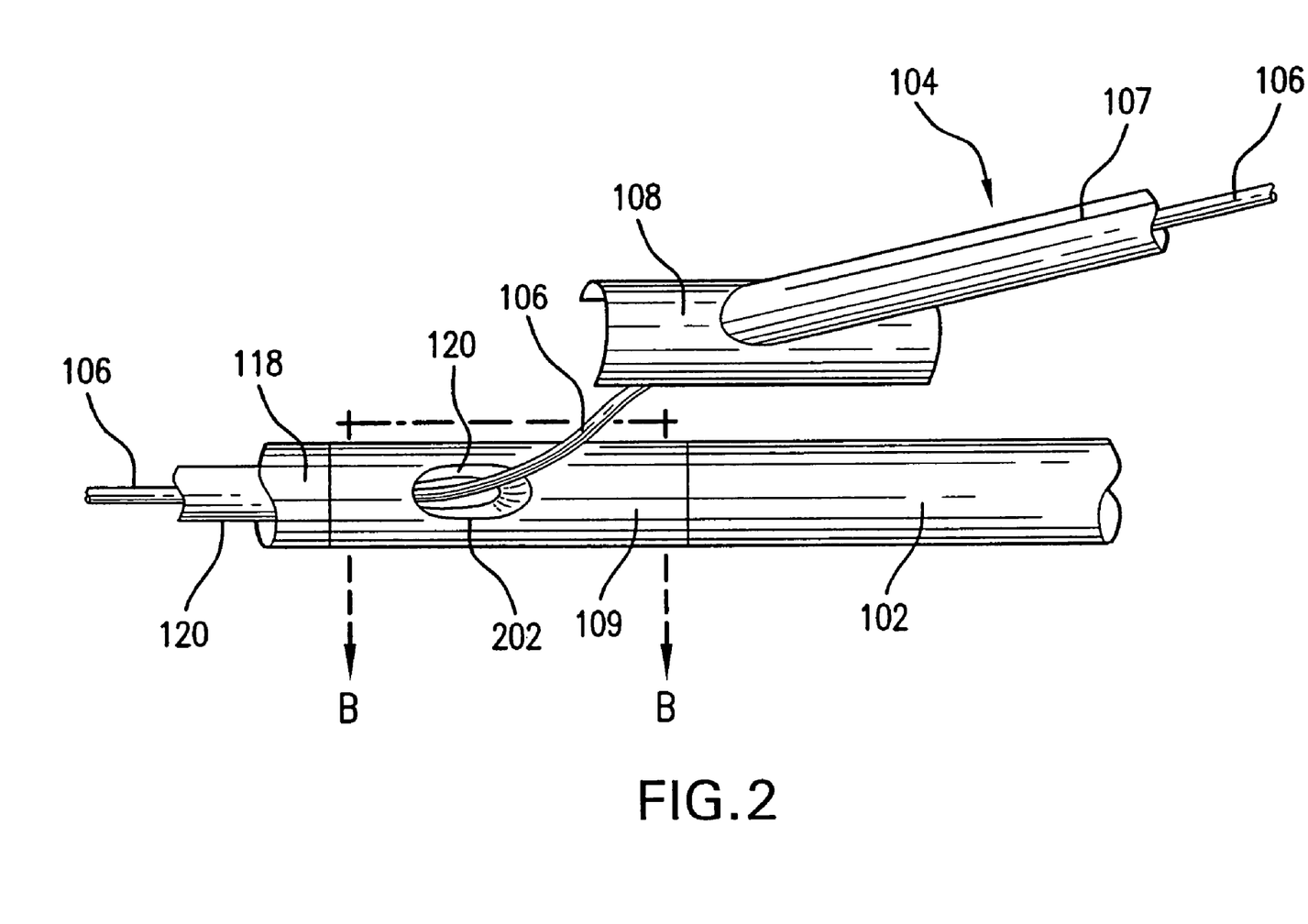
FIG. 2 is an exploded view along line C-C in FIG. 1 of a portion of the catheter in FIG. 1.
Figure 3:
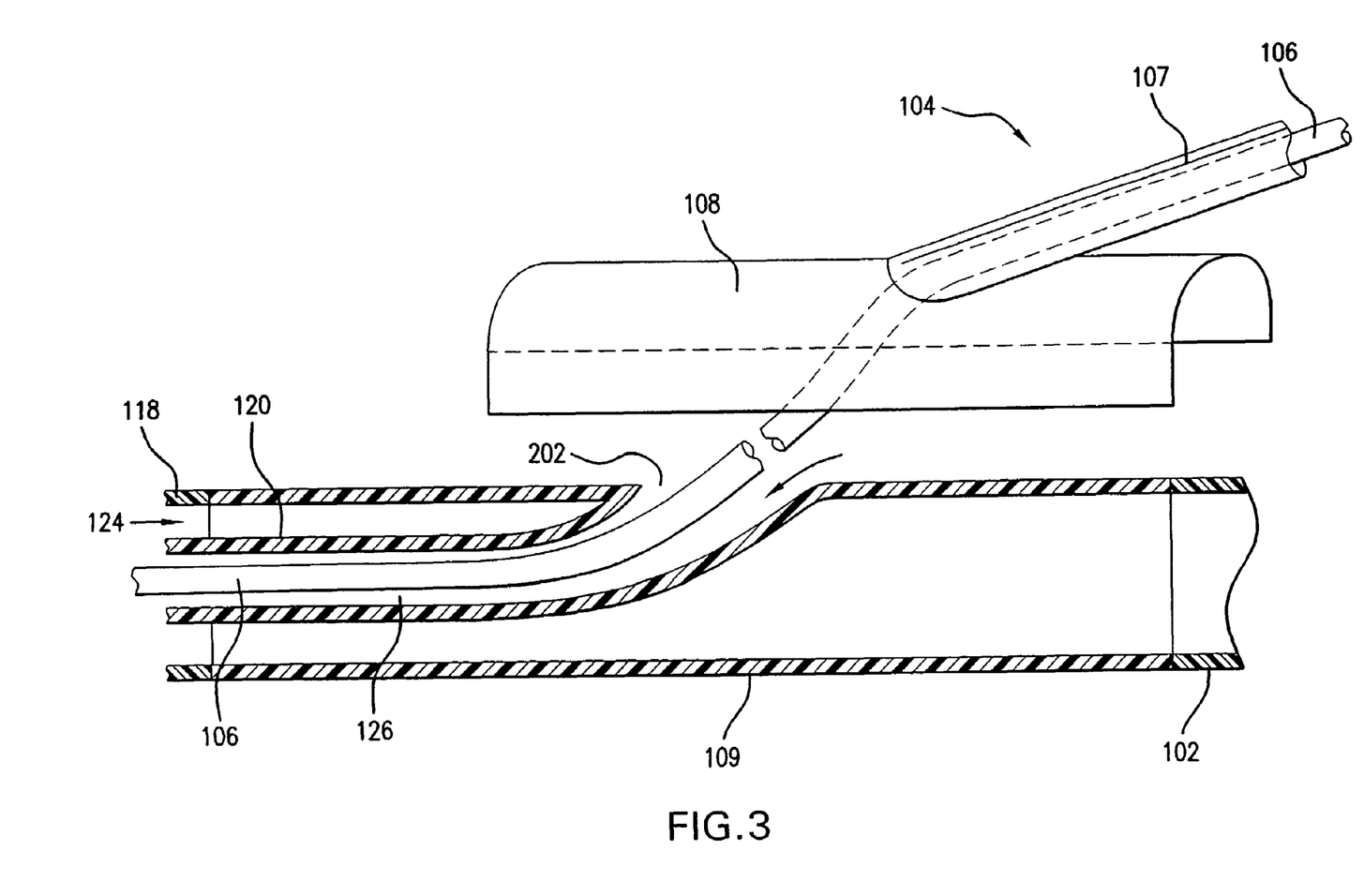
FIG. 3 is a sectional view along line B-B in FIG. 2 with a superimposed enlarged view of a clip and catheter conversion shaft.

Referring to FIGS. 1-3, a preferred embodiment of catheter 100 according to the present invention is shown. Catheter 100 is depicted having an inflation hub 122 attached to a proximal end of a proximal shaft 102. Proximal shaft 102 has an inflation lumen and is attached at a distal end thereof to a proximal end of a transition shaft 109. Transition shaft 109 has an inflation lumen and an exchange joint 202 and is attached at a distal end to a distal shaft 118. With reference to FIG. 1A, distal shaft 118 has an inflation lumen 124, a guidewire shaft 120, and a guidewire lumen 126. A balloon 114 is attached to a distal end of distal shaft 118. Proximal shaft 102, transition shaft 109, and distal shaft 118 together create catheter shaft 101. Inflation hub 122 and the inflation lumens of proximal shaft 102, transition shaft 109, and distal shaft 118 are fluidly connected to each other and to balloon 114, such that an inflation fluid (not shown) can be fluidly communicated therethrough.

Proximal shaft 102 is manufactured from a relatively stiff material (e.g. 304 stainless steel hypotube). Transition shaft 109 and distal shaft 118 are manufactured from any of the following materials: polyethylene terephalate (PET), nylon, and polyethylene. Guidewire shaft 120 is manufactured from, for example, HDPE, polyethylene, PEBAX, nylon or combinations of any of these.

To manufacture catheter 100, proximal shaft 102, transition shaft 109 and distal shaft 118 are bonded to one another. The shafts are secured using a heat or ultrasonic weld or an adhesive treatment as would be known to one of ordinary skill in the art. To ensure a smooth transition between the various shaft portions and to maintain lumens in the bond areas for a guidewire and an inflation fluid, support mandrels and/or wires are placed within each shaft to traverse the bonding areas to ensure that the guidewire lumen and the inflation lumen and the exchange joint remain open.

As shown in FIGS. 1-3, catheter 100 further includes a catheter conversion shaft 104. Catheter conversion shaft 104 has a cut 107 that extends longitudinally along catheter conversion shaft 104 and that extends radially from an inner surface to an outer surface of catheter conversion shaft 104. Attached to a proximal end of catheter conversion shaft 104 is a stop 112. Stop 112 is attached at a distal end to catheter conversion shaft 104 and has an outer diameter that is larger than an outer diameter 119 of catheter conversion shaft 104. Additionally, the stop outer diameter is larger than an inner diameter 117 of a guide member 110 (described below).

Figure 4:
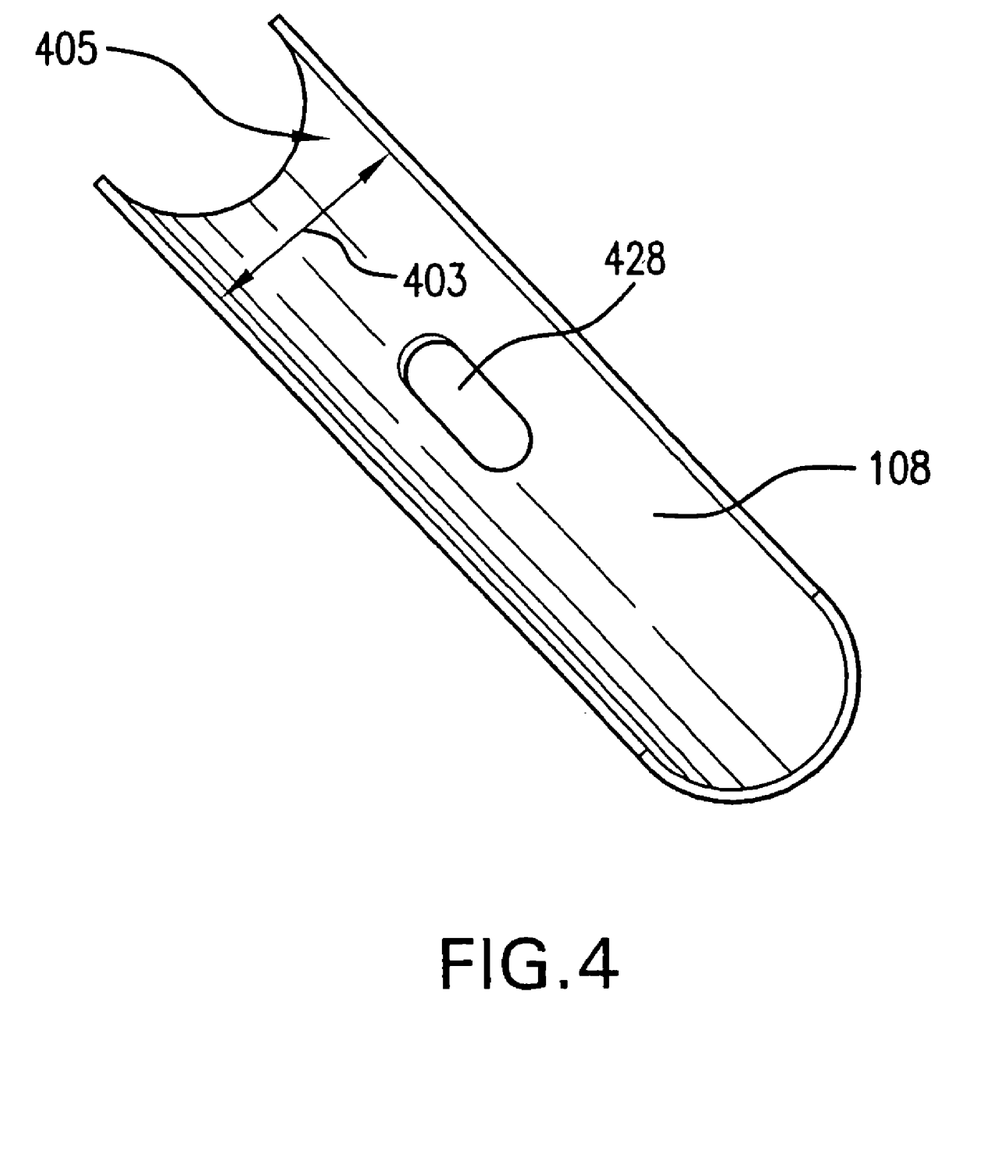
FIG. 4 is a bottom view of the clip shown in FIGS. 1-4.

Attached to a distal end of catheter conversion shaft 104 is a clip 108. As shown in FIGS. 2 and 3, clip 108 is attachable to and detachable from transition shaft 109. As shown in FIG. 4, clip 108 has a clip port 428 that when aligned with exchange joint 202 allows a guidewire 106 to pass therethrough.

Slidably attached to catheter conversion shaft 104 is a guide member 110. Guide member 110 has a guidewire exit 116, which allows a guidewire 106 to pass therethrough. Additionally, guide member 110 has an inner diameter 117, which is greater than an outer diameter 119 of catheter conversion shaft 104. Guide member 110 cooperates with cut 107 in catheter conversion shaft 104 such that guidewire 106 may extend transversely into or out of a guidewire lumen of catheter conversion shaft 104 at any location along the cut's longitudinal length.

Figure 1B:
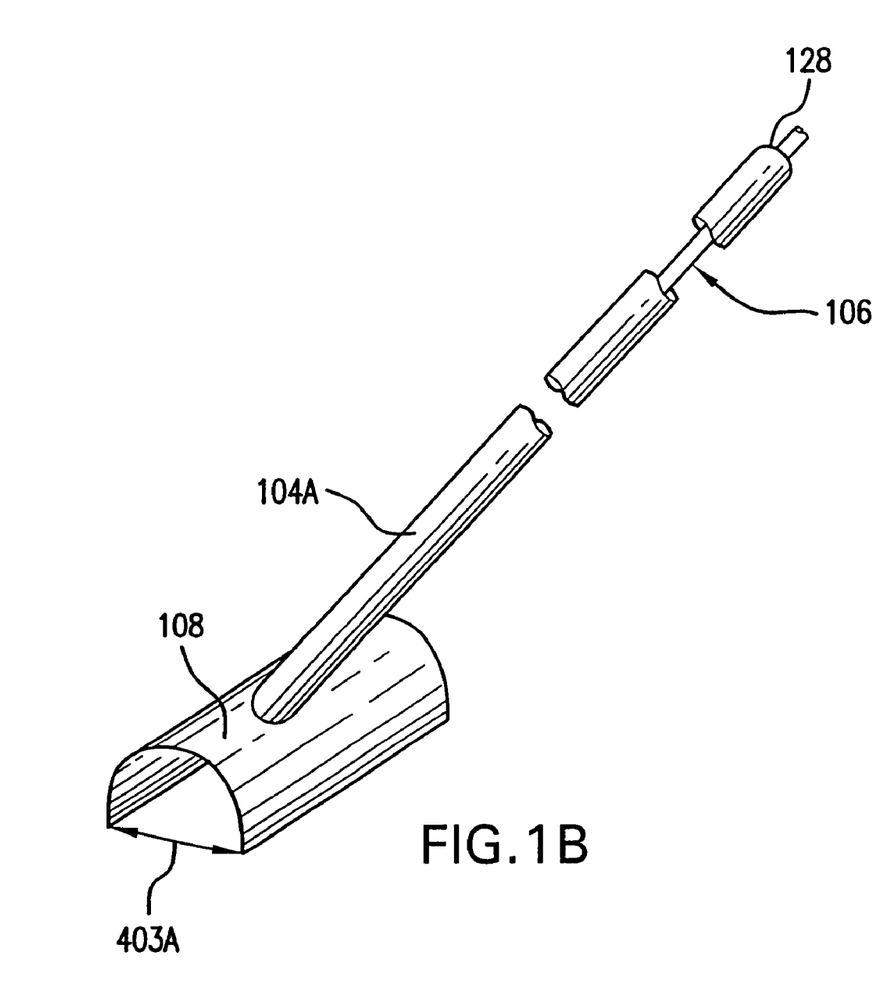
FIG. 1B is an alternate embodiment of the catheter conversion shaft of FIG. 1.

An alternate embodiment of a catheter conversion shaft according to the present invention is shown in FIG. 1B. Catheter conversion shaft 104A includes clip 108 attached to a distal end thereof. Additionally, catheter conversion shaft 104A includes a guidewire lumen extending therethrough from a clip port (not shown) of clip 108 to a proximal opening 128 at a proximalmost end of catheter conversion shaft 104A. Further, guidewire 106 may be accessed at the clip port and at proximal opening 128 of the catheter conversion shaft. Clip inner diameter 403A may be sized and adapted to attach to the proximal guidewire port of any model of a RX catheter so that catheter conversion shaft 104A may be used "off the shelf" when a clinician needs to perform a guidewire exchange. Simlarly, clip 108 of catheter conversion shaft 104 shown in FIG. 1 can be adapted to attach a catheter conversion shaft according to the embodiment of FIG. 1 to the proximal guidewire port of any model of RX catheter.

In this way, the RX catheter's guidewire lumen is extended the entire length of the catheter and in essence converts the RX catheter to an OTW catheter. This allows the RX catheter to remain in place during a guidewire exchange. In order to perform a guidewire exchange utilizing this embodiment, the clinician first slides catheter conversion shaft 104A onto the proximal end of the guidewire and advances it over the guidewire until it "snaps" onto the RX catheter shaft over its proximal guidewire port. Next, the clinician exchanges the indwelling guidewire and then removes the catheter conversion shaft upon completion.

Catheter conversion shafts 104 and 104A are manufactured from, for example, HDPE, polyethylene, PEBAX, nylon or combinations of any of these. A support mandrel is placed within catheter conversion shaft 104 during formation of cut 107. With the mandrel in place, cut 107 may be formed using either a single, moveable blade, a "collet"-type arrangement of numerous blades, or by directional laser. After cut 107 is formed, the guide mandrel is removed. Clip 108 and stop 112 are bonded to catheter conversion shaft 104 in any manner known by one skilled in the art. Again, a support mandrel or wire may be placed in the clip port to ensure that it remains open during bond formation.

One embodiment of a cross-sectional view of distal shaft 118 is shown in FIG. 1A. Distal shaft 118 is comprised of an inflation lumen 124, guidewire shaft 120, and a guidewire lumen 126. An inner surface of distal shaft 118 and an outer surface of guidewire shaft 120 form inflation lumen 124. An inner surface of guidewire shaft 120 forms guidewire lumen 126. In another embodiment, distal shaft 118 may have a noncoaxial guidewire and inflation lumen arrangement.

FIG. 2 is an exploded view along line C-C in FIG. 1 showing a portion of catheter 100 in FIG. 1. As shown in FIG. 2, transition shaft 109 has exchange joint 202, which is an opening through the outer wall of transition shaft 109. Attached to an inner surface of transition shaft 109 around a periphery of exchange joint 202 is a proximal end of guidewire shaft 120. In this way, guidewire lumen 126 is accessible through exchange joint 202. Further, this arrangement allows guidewire 106 to slide into and out of guidewire lumen 126 through exchange joint 202. As seen here in exploded view, guidewire 106 passes through distal shaft 118, transition shaft 109, and exchange joint 202 and into clip 108, and further through catheter conversion shaft 104.

Catheter conversion shaft 104 allows for changing out guidewire 106 while maintaining catheter 100 in situ. To perform the guidewire exchange, with the guidewire position maintained, a proximal end of guidewire 106 is inserted into clip port 428 of clip 108 and walked through catheter conversion shaft 104 and out through guidewire exit 116 of guide member 110. Once the proximal end of guidewire 106 clears guidewire exit 116 and is controlled by the user proximal of guidewire exit 116, catheter conversion shaft 104 is tracked over guidewire 106 and frictionally "clipped" in place to transition shaft 109. In this way, the user is ensured that clip port 428 and exchange joint 202 are aligned and guidewire 106 may pass therethrough. Once attached, guidewire 106 is removed and a new guidewire is inserted into guidewire exit 116 and tracked to the treatment side.

Once the guidewire exchange is complete, catheter conversion shaft 104 is detached by simply pulling free and removed.

Catheter conversion shaft 104A also allows for changing out guidewire 106 while maintaining catheter 100 in situ. To perform the guidewire exchange, the same steps as described above with reference to catheter conversion shaft 104 are followed. However, the proximal end of guidewire 106 is tracked through the entire guidewire lumen of catheter conversion shaft 104A and out through proximal opening 128. Additionally, a new guidewire is inserted into proximal opening 128 of catheter conversion shaft 104A, rather than into a guide member.

FIG. 3 is a sectional view taken along line B-B of FIG. 2 with a superimposed view of clip 108 and catheter conversion shaft 104. Shown here is guidewire shaft 120 attached to the inner surface of transition shaft 109 around a periphery of exchange joint 202. In this way, guidewire lumen 126 is in communication with exchange joint 202, allowing guidewire 106 to slide into and out of guidewire shaft 120 at this point. From exchange joint 202 proceeding distally, guidewire shaft 120 is enveloped by and/or concentric with distal shaft 118 with inflation lumen 124 defined by an outer surface of guidewire shaft 126 and an inner surface of distal shaft 118. From exchange joint 202 proceeding proximally, the inner surface of transition shaft 109 continues the inflation lumen of proximal shaft 102. Additionally, depicted here is the path of guidewire 106 as it passes through exchange joint 202 and clip 108, and into catheter conversion shaft 104.

As shown in FIG. 4, clip 108 has clip port 428. Clip port 428 allows a guidewire to pass therethrough. When clip 108 is attached to transition shaft 109, clip port 108 is aligned with exchange joint 202. Also shown here is clip inner diameter 403 and clip inner surface 405. Inner diameter 403 is substantially similar in size to transition shaft outer diameter 103. In this way, when clip 108 is attached to transition shaft 109, friction created between clip surface 405 and transition shaft outer surface 105 holds clip 108 in place.

Additionally, clip 108 may be designed and manufactured with various inner diameter sizes. The catheter conversion shaft may then be used as a separate component with any off the shelf RX catheter model. In this way, the variable widths account for variable shaft outer diameters adjacent the proximal guidewire ports of any RX catheter and ensure clip 108 stays attached thereto.

Figure 5:
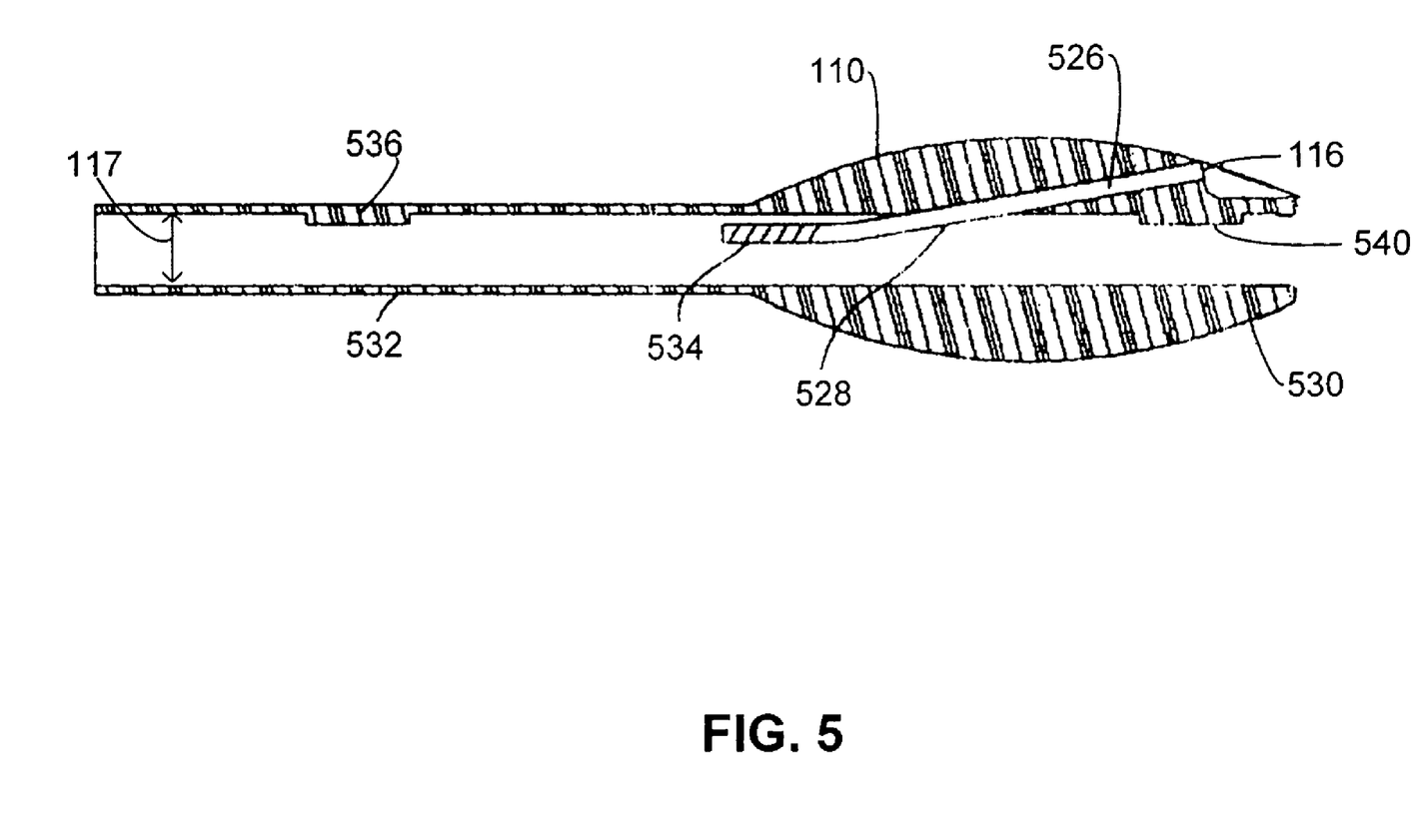
FIG. 5 is a sectional view along line D-D of FIG. 1.

FIG. 5 depicts a sectional view of guide member 110, taken along line D-D in FIG. 1 with guidewire 106 and catheter conversion shaft 104 not shown. Guide member 110 includes guidewire exit 116 for guidewire 106 to enter and exit catheter conversion shaft 104. Guide member 110 comprises a proximal portion 530, a proximal spreader 540, a distal portion 532, a distal spreader 536, a guidewire passageway 526, and a guidewire tube 528 having, for example, a spiral distal end 534. Spiral distal end 534 may be curved into alignment with the guidewire lumen of catheter conversion shaft 104.

Guidewire exit 116 is located in a scallop-shape recession formed in guide member proximal portion 530 to aid insertion of a tip of guidewire 106. Additionally, guidewire tube 528 extends distally from guidewire exit 116 to intersect the guidewire lumen in catheter conversion shaft 104 at a shallow angle, preferably in a coaxial relationship with the guidewire lumen. Once the tip of guidewire 106 is inserted into guidewire exit 116, guidewire 106 passes through guidewire passage 526 in guidewire tube 528, and into the guidewire lumen of catheter conversion shaft 104.

To ensure guidewire tube 528 passes through longitudinal cut 107, spreaders 536 and 540 are sized to open cut 107 as guide member 110 slides along catheter conversion shaft 104. Once guide member 110 has passed, the inherent resiliency of catheter conversion shaft 104 closes cut 107 thus enclosing guidewire 106 in the catheter conversion shaft guidewire lumen. Spreaders 536 and 540 are formed in the body of guide member 110. Spreaders 536 and 540 also act to align guidewire tube 528 with cut 107. Inner diameter 117 is sized such that guide member 110 may easily slide over catheter conversion shaft 104.

In one embodiment, to construct guide member 110, guide member 110 is molded from a suitable rigid plastic material, such as nylon, or acrylonitrile-butadiene-styrene (ABS) material. Alternatively, guide member 110 may be made of a suitable metal such as stainless steel or guide member 110 may have both metal components and plastic components. For ease of manufacturing, guide member 110 may be comprised of molded parts that snap fit together. Guidewire tube 528 is made from 304 stainless steel hypotube or a strong, thin-walled polymer, such as thermoset polyimide (PI) tubing or other comparable materials. Guidewire tube 528 may be fixed or slidably disposed in guidewire passageway 526.

FIGS. 6 through 10 show an alternate embodiment of a guide member 610. In this instance, guide member 610 surrounds catheter conversion shaft 104 and has a proximal portion 692 and a distal portion 694. Guide member 610 has an outer tubular member 696 that freely rotates around inner main body 698 and is therefore rotatably coupled to inner main body 698. A stop positioned on distal portion 694 consists of an annular wall 700 radially extending into a distal opening 702 of outer member 696 and prevents main body 698 from slipping out of the outer tubular member 696. A retaining clip mechanism 604 is positioned on proximal portion 692.

Figure 6:
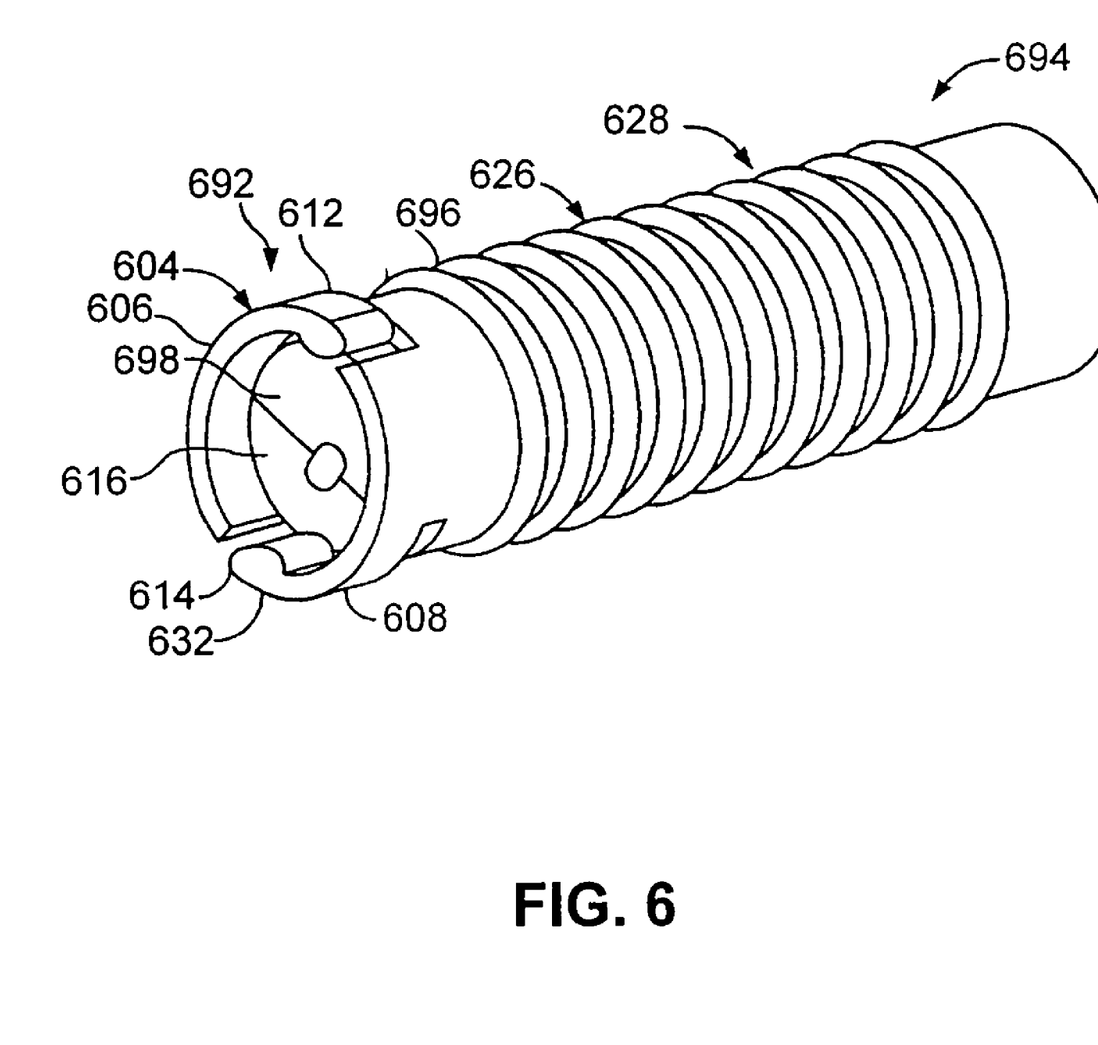
FIGS. 6 and 7 are perspective views of a second embodiment of a guide member.
Figure 7:
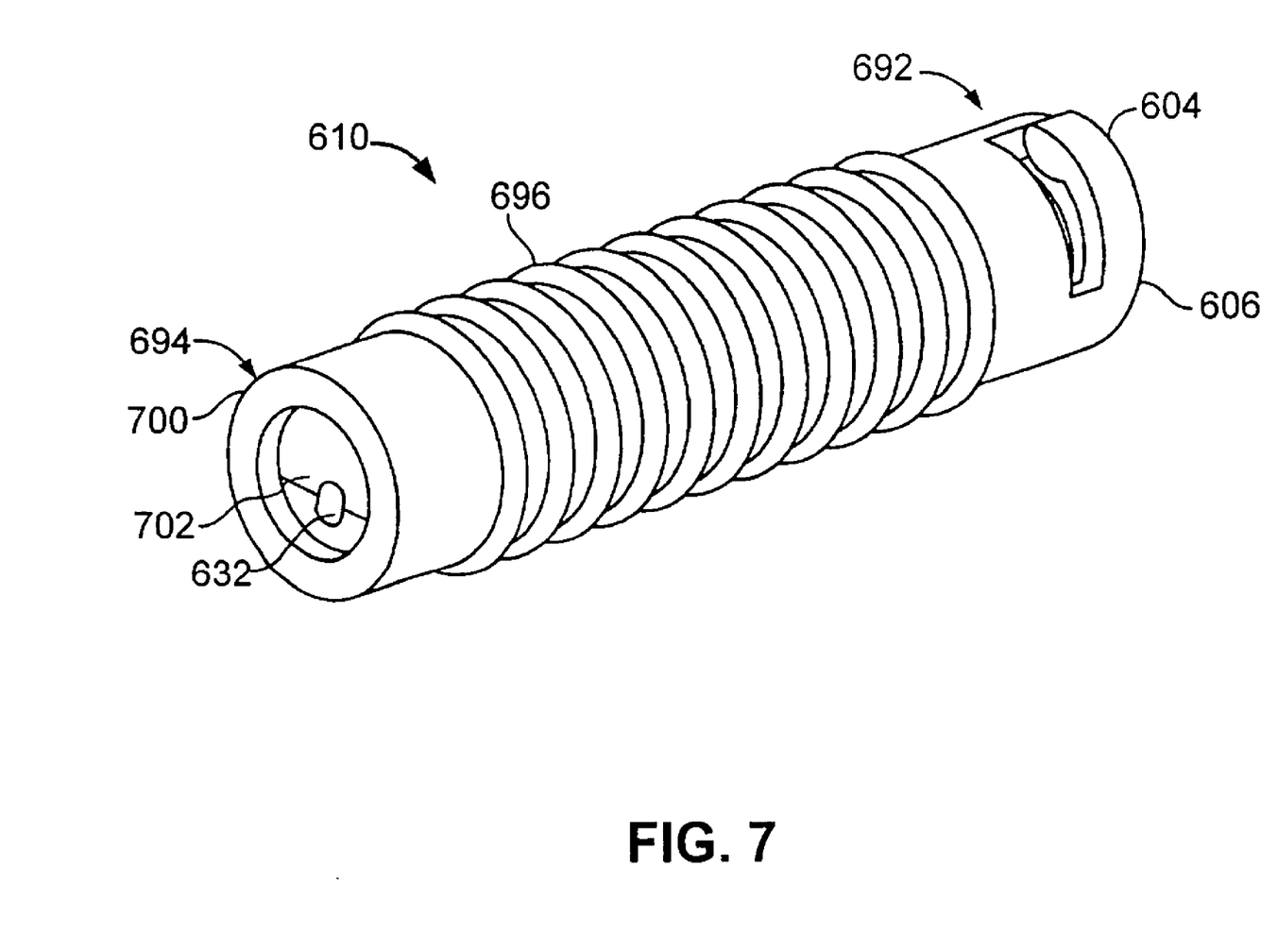

Retaining clip mechanism 604 consists of two arcuate arms 606 and 608 that form a portion of outer member 696. Each arm contains a tab 612 and 614 respectively, that extends into a proximal opening 616 of outer tubular member 696 to prevent main body 698 from slipping out of outer tubular member proximal opening 616. Arms 606 and 608 are opened up to remove tabs 612 and 614 from extending into proximal opening 616 to permit insertion of main body 698 during the assembly of guide member 610. While the two tabs are shown positioned 180 degrees apart, a different number of tabs may be used, provided they are spaced sufficiently to prevent main body 698 from slipping out of outer member 696.

An outer surface 626 of guide member 610 may have a textured surface to include a plurality of circumferential bosses 628 to assist in grasping and manipulating guide member 610 and to prevent slipping as catheter conversion shaft 104 is advanced through guide member 610. An inner surface (not shown) of outer tubular member 696 is smooth to facilitate rotation around inner main body 698. Furthermore, the materials used to manufacture guide member 610 may be chosen for their friction reducing ability and a coating may be applied on the inner surface to also reduce friction.

Figure 8:
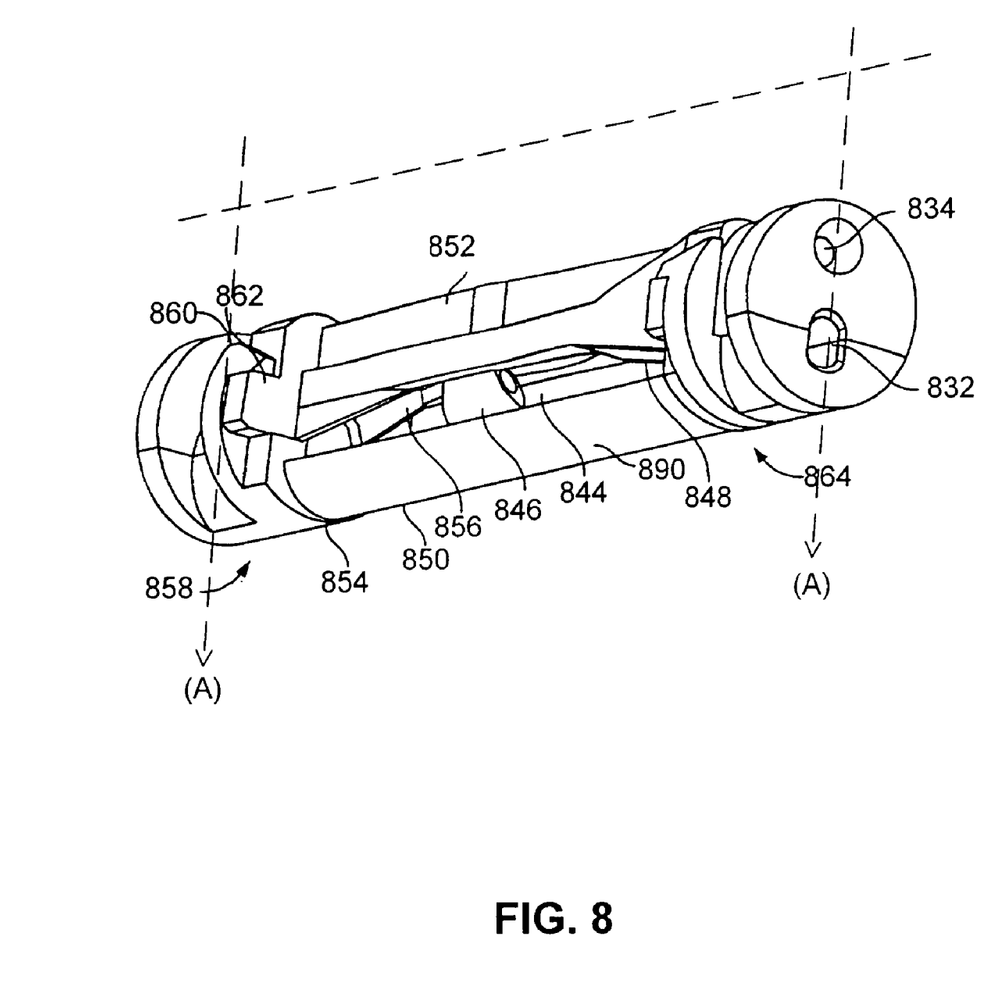
FIG. 8 is a perspective view of a main body portion of the guide member of FIGS. 6 and 7.

Guide member main body 698 is constructed from two parts, a top 852 and a base 854, as seen in FIG. 8. Guide member main body 698 houses a guidewire passageway 834, a catheter shaft passageway 632, a keel 846, a tube (not shown), and a plurality of guideway closing aids 848 and 856. Base 854 forms a shaft support channel 850. Clipping mechanisms 858 and 864 are used to secure top 852 and base 854. A snap fit assembly is preferable for ease of assembly while still assuring top 852 and base 854 are aligned when secured. In particular, clipping mechanism 858 consists of an arcuate arm 860 extending from base 854 that engages arm 862 formed on top 852. Clipping mechanism 864 operates in the same fashion. Four clipping mechanisms ensure a secure fit and thus additional clipping mechanisms (not shown) are located opposite clipping mechanisms 858 and 864.

Figure 9:
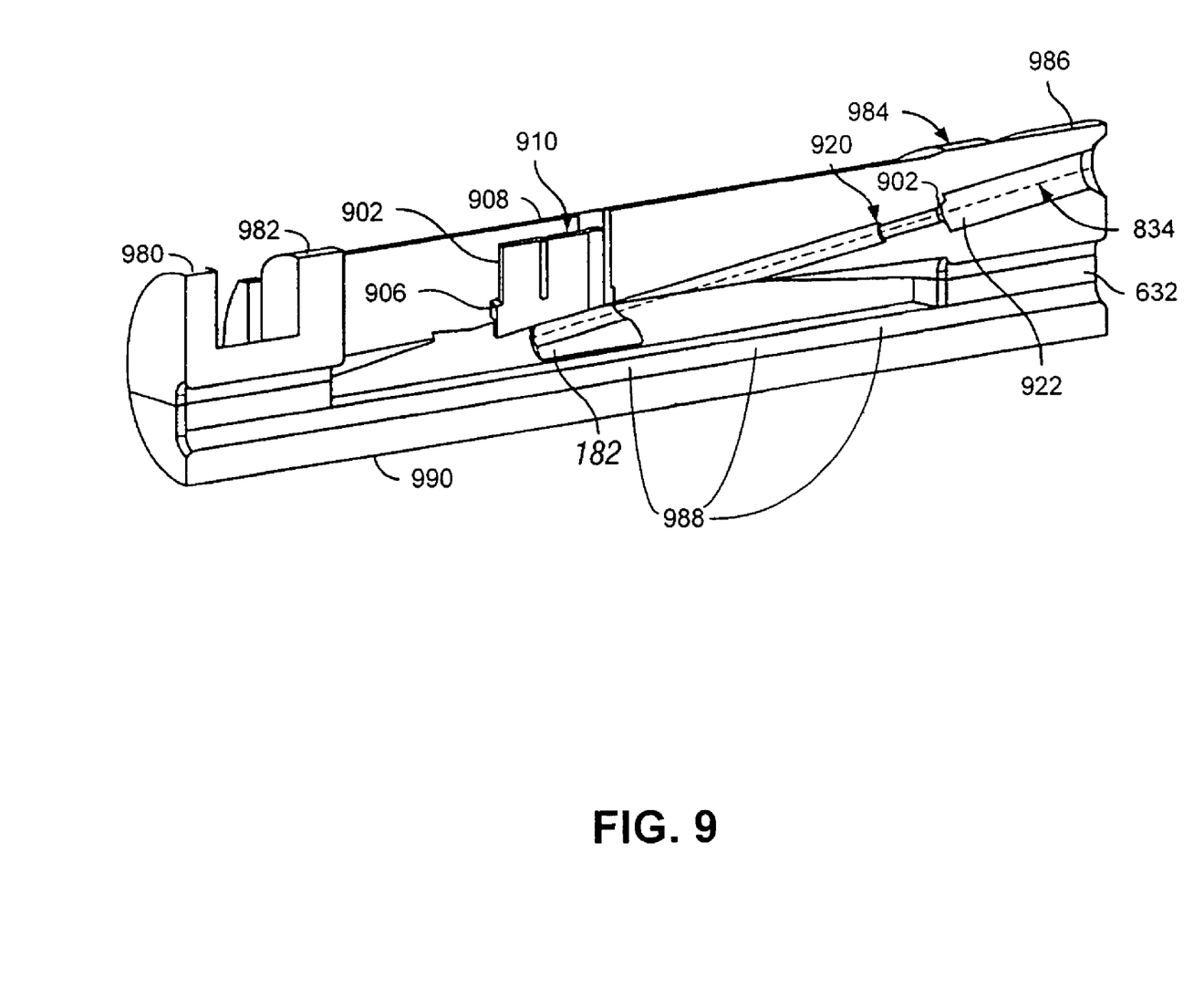
FIG. 9 is a cut-away view along line A-A of FIG. 8

Further, guide member main body 698 contains a plurality of arcuate surfaces 980, 982, 984, and 986 that form outer bearing surfaces that contact inner surface of rotating outer tubular member 696. A support channel 988 is formed along a bottom of catheter passageway 632 and holds, for example, catheter conversion shaft 104 under keel 846. A support channel outer surface 990 is also in bearing contact with the inner surface of outer tubular member 696. Outer surface 990, along with surfaces 980, 982, 984, and 986 are smooth to reduce any frictional forces caused by rotating outer member 696 about main body 698. A clearance of approximately 0.05 mm exists between the inner and outer surfaces.

Figure 10:
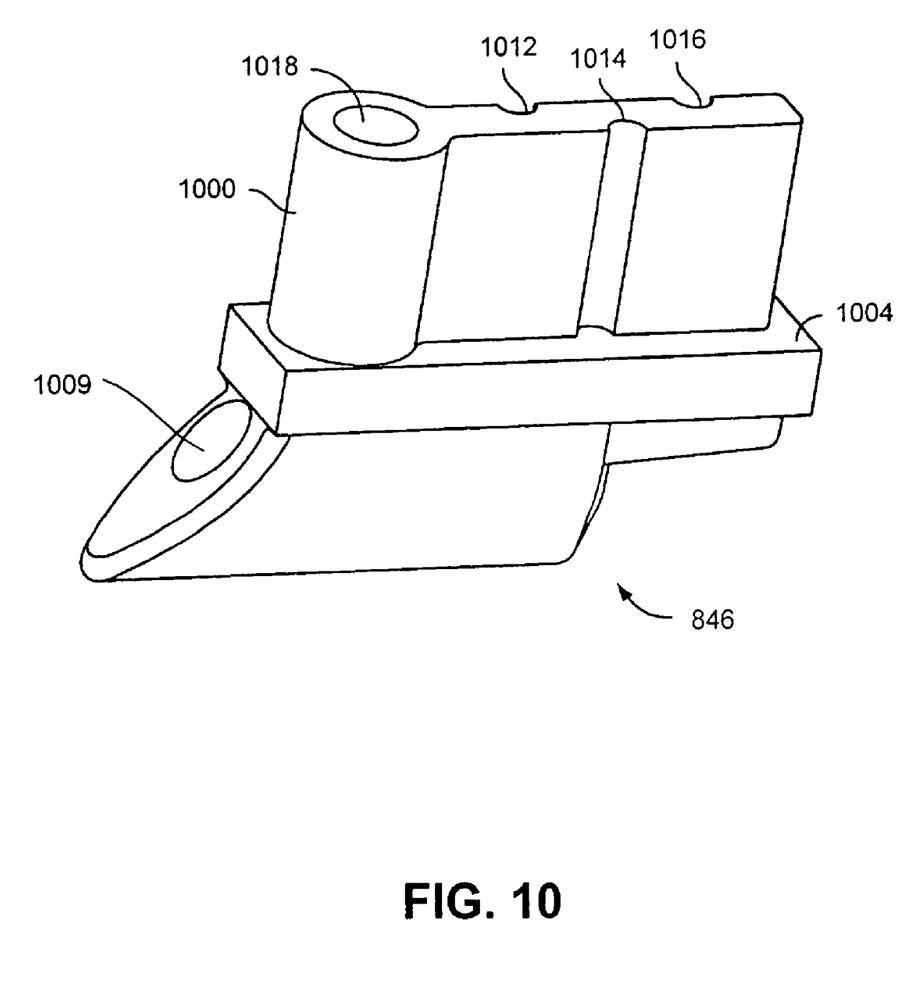
FIG. 10 is a perspective view of a keel portion of the guide member shown in FIGS. 8 and 9.

Keel 846 is formed preferably as a separate component from main body 698 to allow more flexibility in the keel design. The size, shape, and material of keel 846 will not be limited by the manufacture of main body 698. Keel 846 contains an upper portion 1000 that is designed to mate with slot 902 in top 852. A positive stop, shoulder 1004 surrounds upper portion 1000 and mates with a ledge 906 of slot 902. Once mated, a keel passageway 1009 is in proper alignment with a guidewire passageway 834 extending through top 852. Upper portion 1000 does not extend to be flush with outer surface 908 of top 852 thereby forming a recess 910. A plurality of adhesive channels 1012, 1014, and 1016 extend along the sides of upper portion 1000. A bore 1018 extends through upper portion 1000 and into keel passageway 1009.

Keel 846 is preferably secured to top 852 with an adhesive. Keel 846 is inserted into slot 902 until shoulder 1004 is firmly seated against ledge 906. Once seated, passageways 1009 and 834 are aligned so that the tube may be inserted. Passageway 834 contains a stop 920 just prior to an area 922 that receives a wire introducer tool (not shown). The tube is seated in place once it abuts stop 920. An adhesive is then placed in channels 1012, 1014, and 1016 securing keel 846 to top 852. Adhesive is also placed in bore 1018 that extends down to the tube. Any excess adhesive will pool in recess 910 and not interfere with fitting the various components of guide member 610 together.

Catheter 100 is designed to be used as both a rapid-exchange catheter when catheter conversion shaft 104 is not attached and as a multi-exchange catheter when catheter conversion shaft 104 is attached. With guidewire 106 and catheter 100 configured as a rapid-exchange catheter, a procedure begins by first tracking guidewire 106 to a treatment site. Once guidewire 106 is in place, a proximalmost tip of guidewire 106 is inserted into a distalmost tip of guidewire shaft 120 of catheter 100. Guidewire 106 passes through guidewire lumen 126 and exchange joint 202. Holding guidewire 106, catheter 100 is advanced into the vasculature.

To replace guidewire 106 with a new guidewire while maintaining catheter position in situ, the proximalmost tip of guidewire 106 is inserted into clip port 428 of catheter conversion shaft 104. Catheter conversion shaft 104 is then tracked over guidewire 106 until guidewire 106 exits the shaft through guidewire exit 116 of guide member 110. In order for the user to maintain control over the guidewire, guide member 110 is slidably positioned along catheter conversion shaft 104 at its distalmost position along cut 107, just proximal of clip 108.

Holding guidewire 106 and guide member 110, catheter conversion shaft 104 is advanced distally over guidewire 106. As the shaft is advanced, guide member 110 moves proximally along cut 107 of catheter conversion shaft 104 thereby enveloping guidewire 106 in catheter conversion shaft 104. Guidewire 106 acts to guide clip 108 into position and acts to self align clip port 428 with exchange joint 202. When clip 108 reaches exchange joint 202, clip 108 attaches onto transition shaft 109. With catheter conversion shaft 104 attached, guidewire 106 may be fully removed by pulling it out through guidewire exit 116 while maintaining catheter 100 in situ. Once guidewire 106 is fully removed, a new guidewire may be introduced into guidewire exit 116 and tracked in place.

Once the new guidewire is in place, catheter conversion shaft 104 is detached from transition shaft 109 and withdrawn. To maintain guidewire position, the new guidewire and guide member 110 are controlled as catheter conversion shaft 104 is tracked off the new guidewire. In doing so, guide member 110 moves distally along cut 107 of catheter conversion shaft 104. Once guide member 110 is in its distalmost position, the new guidewire will be visible distal of clip 108 and control of the guidewire will be switched to distal of clip 108. The new guidewire is controlled as catheter conversion shaft 104 is fully removed.

While this invention has been particularly shown and described with reference to preferred embodiments thereof, it will be understood by those skilled in the art that various changes in form and details may be made therein without departing from the spirit and scope of the invention.

What is claimed is:

1. A catheter comprising:

a proximal shaft having a proximal end, a distal end and an inflation lumen;

a distal shaft indirectly connected at a proximal end to the distal end of the proximal shaft and having an inflation lumen in fluid communication with the inflation lumen of the proximal shaft, wherein the distal shaft includes a guidewire shaft having a guidewire lumen;

an exchange joint located adjacent the proximal end of the distal shaft for access to the guidewire lumen; and a catheter conversion shaft having a proximal end and a distal end with a guidewire lumen, the catheter conversion shaft having a clip portion at the distal end thereof for detachably securing the catheter conversion shaft over the exchange joint of the catheter such that the guidewire lumen thereof is in communication with the guidewire lumen of the distal shaft wherein the exchange joint is located in a transition shaft of the catheter that includes an outer surface and an outer diameter, wherein the clip portion includes an inner surface and an inner diameter, wherein the inner diameter of the clip portion and the outer diameter of the transition shaft are substantially the same size, such that the clip portion of the catheter conversion portion may be frictionally fit on the transition shaft of the catheter.

2. The catheter of claim 1, wherein the catheter conversion shaft includes a guidewire exit for access to the guidewire lumen of the catheter conversion shaft.

3. The catheter of claim 2, wherein the guidewire exit comprises a guide member that is slidable on the catheter conversion shaft.

4. The catheter of claim 3, wherein the catheter conversion shaft further includes a longitudinal cut that allows access to the guidewire lumen via the slidable guide member.

5. The catheter of claim 1, wherein the outer surface of the transition shaft is in contact with the inner surface of the clip portion when the catheter conversion shaft is attached to the transition shaft.

6. The catheter of claim 1, wherein a frictional fit secures the clip portion of the catheter conversion shaft in place over the exchange joint.

7. The catheter of claim 1, wherein the clip portion includes an inner surface and an inner diameter, wherein the inner diameter comprises one of a plurality of variable sizes.

8. The catheter of claim 7, wherein the catheter may be any RX catheter model.

* * * * *